United States Patent
Guiney et al.

(10) Patent No.: US 11,850,327 B2
(45) Date of Patent: Dec. 26, 2023

(54) FLEXIBLE HEXAGONAL BORON NITRIDE COMPOSITES FOR ADDITIVE MANUFACTURING APPLICATIONS

(71) Applicant: Northwestern University, Evanston, IL (US)

(72) Inventors: Linda M. Guiney, Chicago, IL (US); Nikhita D. Mansukhani, Libertyville, IL (US); Adam E. Jakus, Chicago, IL (US); Ramille N. Shah, Hinsdale, IL (US); Mark C. Hersam, Wilmette, IL (US)

(73) Assignee: Northwestern University, Evanston, IL (US)

( * ) Notice: Subject to any disclaimer, the term of this patent is extended or adjusted under 35 U.S.C. 154(b) by 679 days.

(21) Appl. No.: 17/049,281

(22) PCT Filed: Apr. 30, 2019

(86) PCT No.: PCT/US2019/029902
§ 371 (c)(1),
(2) Date: Oct. 20, 2020

(87) PCT Pub. No.: WO2019/213071
PCT Pub. Date: Nov. 7, 2019

(65) Prior Publication Data
US 2021/0038770 A1    Feb. 11, 2021

Related U.S. Application Data (60) Provisional application No. 62/664,733, filed on Apr. 30, 2018.

(51) Int. Cl.
*A61F 2/28* (2006.01)
*A61L 27/44* (2006.01)
(Continued)

(52) U.S. Cl.
CPC .............. *A61L 27/446* (2013.01); *A61L 27/50* (2013.01); *A61M 5/14276* (2013.01);
(Continued)

(58) Field of Classification Search
CPC ............... A61L 27/50; C08K 2201/013; C08L 2314/00; C08L 2666/46; A61F 2002/286
See application file for complete search history.

(56) References Cited

U.S. PATENT DOCUMENTS

| 8,287,895 B1 | 10/2012 | Kisailus et al. |
| 2015/0202351 A1 | 7/2015 | Kaplan et al. |
| 2017/0081534 A1 | 3/2017 | Shah et al. |

FOREIGN PATENT DOCUMENTS

WO    WO 2017/021936 A1    2/2017

OTHER PUBLICATIONS

Shahriar Ghaffari Mosanenzadeh et al., "High Thermally Conductive PLA-Based Composites with Tailored Hybrid Network of Hexagonal Boron Nitride and Graphene Nanoplatelets," *Polym. Compos.* 2015, 37, 2196-2205.
(Continued)

*Primary Examiner* — Deanna K Hall
(74) *Attorney, Agent, or Firm* — Bell & Manning, LLC (57) ABSTRACT

Thermal management composites and scaffolds for heat-generating implantable electronic devices made from the thermal management composites are provided. The composite materials are cytocompatible, porous materials that include hexagonal boron nitride particles dispersed in an elastomeric polymer binder.

10 Claims, 8 Drawing Sheets

(51) Int. Cl.
- B33Y 80/00 (2015.01)
- A61N 1/375 (2006.01)
- B33Y 70/10 (2020.01)
- A61L 27/50 (2006.01)
- A61M 5/142 (2006.01)
- C08K 3/38 (2006.01)
- D01F 1/10 (2006.01)
- D01F 6/62 (2006.01)
- D01F 6/84 (2006.01)
- D01F 6/92 (2006.01)

(52) U.S. Cl.
CPC .......... *A61N 1/37512* (2017.08); *B33Y 70/10* (2020.01); *B33Y 80/00* (2014.12); *C08K 3/38* (2013.01); *D01F 1/10* (2013.01); *D01F 6/625* (2013.01); *D01F 6/84* (2013.01); *D01F 6/92* (2013.01); *A61M 2205/3633* (2013.01); *C08K 2003/385* (2013.01)

(56) References Cited

OTHER PUBLICATIONS

Conor S. Boland et al., "High stiffness nano-composite fibres from polyvinylalcohol filled with graphene and boron nitride," *Carbon*, vol. 99, 2016, pp. 280-288.

Xieliang Cui et al., "Thermal Conductive and Mechanical Properties of Polymeric Composites Based on Solution-Exfoliated Boron Nitride and Graphene Nanosheets: A Morphology-Promoted Synergistic Effect," *ACS Appl. Mater. Interfaces*, 2015, vol. 7, pp. 19068-19075.

Cheng Zhu et al., "Supercapacitors Based on Three-Dimensional Hierarchical Graphene Aerogels with Periodic Macropores," *Nano Lett.* 2016, vol. 16, pp. 3448-3456.

Wei-Li Song et al., "Polymer/Boron Nitride Nanocomposite Materials for Superior Thermal Transport Performance," *Angew. Chem. Ed.* 2012, vol. 124, pp. 6604-6607.

Zhiqiao Kuang, "Fabrication of Highly Oriented Hexagonal Boron Nitride Nanosheet/Elastomer Nanocomposites with High Thermal Conductivity," *Small* 2015, 11, 1655-1659.

Chunyi Zhi et al., "Large-Scale Fabrication of Boron Nitride Nanosheets and Their Utilizaion in Polymeric Composites with Improved Thermal and Mechanical Properties," *Adv. Mater.* 2009, 21, 2889-2893.

Qunhong Weng et al., "Highly.Water-Soluble, Porous, and Biocompatible Boron Nitrides for Anticancer Drug Delivery," *ACS Nano* 2014, vol. 8, No. 6, pp. 6123-6130.

New technique produces longer-lasting lithium batteries, ScienceDaily, Columbia University Schoolof Engineering and Applied Science, Apr. 22, 2019, pp. 1-4.

Stefano Moscato et al., "Infill-Dependent 3-D-Printed Material Based on NinjaFlex Filament forAntenna Applications," IEEE Antennas and Wireless Propagation Letters, vol. 15, 2016, pp. 1506-1509.

Gaurav Lalwani et al., "Two-Dimensional Nanostructure-Reinforced Biodegradable Polymeric Nanocomposites for Bone Tissue Engineering," Biomacromolecules, Mar. 11, 2013, vol. 14, No. 3, pp. 900-909. Doi: 10.1021/bm301995s.

Manuela Loeblein et al., "High-Density 3D-Boron Nitride and 3D-Graphene for High-Performance Nano-Thermal Interface Material," ACS Nano, vol. 11, No. 2, (2017), pp. 1-33.

Adam E. Jakus et al., "Three-Dimensional Printing of High-Content Graphene Scaffolds for Electronic and Biomedical Applications," ACS Nano, 2015, vol. 9, No. 4, pp. 4636-4648.

Esther Garcia-Tunon et al., "Printing in three-dimensions with graphene," Adv. Mater. http://dx.doi.org/10.1002/adma.201405046, pp. 1-14.

Christopher W. Foster et al., "3D Printed Graphene Based Energy Storage Devices," Scientific Reports, 7:42233, DOI:10.1038/srep42233, pp. 1-11.

Behzad Farshid et al., "Boron Nitride Nanotubes and Nanoplatelets as Reinforcing Agents of Polymeric Matrices for Bone Tissue Engineering," J. Biomed. Mater. Res. B. Appl. Biomater., Feb. 2017, vol. 105, No. 2, pp. 406-419. doi:10.1002/jbm.b.33565.

The International Search Report and Written Opinion dated Jul. 29, 2019 for International Patent Application No. PCT/US19/29902, pp. 1-9.

Lahiri et al., "Boron nitride nanotube reinforced polylactide-polycaprolactone copolymer composite : Mechanical properties and cytocompatibility with osteoblasts and macrophages in vitro," Acta Biomaterilia, Mar. 10, 2010, vol. 6, Issue 9, pp. 3524-3533.

Guiney et al., "Three Dimensional Printing of Cytocompatible, Thermally Conductive Hexagonal Boron Nitride Nanocomposites," Nano Letters, Apr. 30, 2018, vol. 18, Issue 6, pp. 3488-3493.

Guiney et al., "Supporting Information—Three Dimensional Printing of Cytocompatible, Thermally Conductive Hexagonal Boron Nitride Nanocomposites," Nano Letters, Apr. 30, 2018, vol. 18, Issue 6, pp. 3488-3493.

Mosanenzadeh et al., "Effect of filler arrangement andnetworking of hexagonal boron nitride on the conductivity of new thermal management polymeric composites," Composites Part B: Engineering, vol. 85, Sep. 26, 2015, pp. 24-30.

Feng et al., "A space network structure constructed by tetraneedle-like ZnO whiskers supporting boron nitride nanosheets to enhance comprehensive properties of poly(L-lactic acid) scaffolds," Scientific Reports, vol. 6, Article 33385, Sep. 15, 2016, pp. 1-15.

Jenniffer Bustillos et al., "Stereolithography-based 3D printed photosensitive polymer/boron nitride nanoplatelets composites," Polymer Composites, Nov. 2017, DOI: 10.1002/pc.24662, pp. 1-11.

Burak Ozbek et al., "Production of the novel fibrous structure of poly(E-caprolactone)/tri-calcium phosphate/hexagonal boron nitride composites for bone tissue engineering," J. Aust. Ceram. Soc. 2017, https://doi.org/10.1007/s41779-017-0149-0, pp. 1-10.

FLEXIBLE HEXAGONAL BORON NITRIDE COMPOSITES FOR ADDITIVE MANUFACTURING APPLICATIONS

CROSS-REFERENCE TO RELATED APPLICATIONS

This application is a National Stage of International Application No. PCT/US19/29902, filed Apr. 30, 2019, which claims the benefit of U.S. Patent Application No. 62/664,733, filed Apr. 30, 2018, the contents of which are herein incorporated by reference.

REFERENCE TO GOVERNMENT RIGHTS

This invention was made with government support under DBI-1266377 and DMR-1720139 awarded by the National Science Foundation. The government has certain rights in the invention.

BACKGROUND

With increasing electronic device density, speed, and power dissipation, thermal management has become a key consideration for integrated circuit technology. Furthermore, as the field moves towards mechanically flexible electronics and roll-to-roll manufacturing techniques, additional constraints such as flexibility, stretchability, weight, and cost are placed upon thermal management materials. These constraints are even more severe in the field of implantable bioelectronics where small changes in temperature can disrupt the normal functions or viability of surrounding tissues.

Three-dimensional (3D) extrusion printing is an additive manufacturing technique that offers many advantages including the ability to produce customized complex objects on demand in addition to the elimination of waste created by subtractive manufacturing techniques such as machining. The ability to rapidly design and fabricate architectures that are not otherwise possible with traditional methods has led to significant growth in the 3D printing field in both the research and industrial communities. However, 3D printing is generally limited by the number and types of materials that are compatible with this method. The majority of 3D printing techniques are restricted to thermoplastics, photopolymers, and metals, which constrains both the mechanical and functional properties of the resulting structures. One approach for overcoming these limitations is to incorporate functional particles into polymer matrices to enhance functionality. The effectiveness of this approach relies on achieving a sufficiently high volume fraction of particles in the polymer matrix to modify targeted properties while still maintaining 3D printability.

Two-dimensional (2D) layered nanomaterials are superlative filler materials for polymer nanocomposites due to their high surface area, exceptional mechanical properties, and broadly tunable electrical, optical, and thermal properties. With these attributes, 2D nanomaterials have yielded improved performance in a wide range of applications in electronic, energy, and biomedical technologies. Recent work has shown successful 3D printing of graphene-polymer nanocomposites with high electrical conductivity that are enabling new applications in printed electronics, energy storage, and tissue engineering. (See, e.g., Jakus, A. E., et al., *ACS Nano* 2015, 9, 4636-4648; Garcia-Tuñon, E., et al., *Adv. Mater.* 2015, 27, 1688-1693; Foster, C. W., et al., *Sci. Rep.* 2017, 7, 42233; and Zhu, C., et al., *Nano Lett.* 2016, 16, 3448-3456.) However, 3D printing of other 2D nanomaterials has been limited due to challenges in realizing 3D printable polymer nanocomposites based on non-carbon 2D nanomaterials.

Previous work has incorporated hexagonal boron nitride (hBN) into polymer nanocomposites in order to enhance thermal conductivity. However, the hBN-polymer nanocomposites to-date possess a trade-off between thermal and mechanical properties, especially in the high hBN loading limit. Furthermore, previously reported hBN-polymer nanocomposites have been primarily prepared using casting procedures that require post-processing steps to manipulate the 3D shape of the final structure.

SUMMARY

Composite materials that include hexagonal boron nitride particles dispersed in a polymeric matrix and continuous, self-supporting, flexible fibers formed by extrusion printing the composite materials are provided. Cytocompatible thermal management scaffolds for heat-generating implantable medical devices made from the composite materials are also provided.

One embodiment of a bioelectronic device includes an implantable electronic device and a thermally conductive, electrically insulating scaffold around at least a portion of the implantable electronic device. The scaffold is composed of one or more struts of a cytocompatible composite that includes a biocompatible elastomeric polymer binder and hexagonal boron nitride particles dispersed in the biocompatible elastomeric polymer binder.

Other principal features and advantages of the invention will become apparent to those skilled in the art upon review of the following drawings, the detailed description, and the appended claims.

BRIEF DESCRIPTION OF THE DRAWINGS

Illustrative embodiments of the invention will hereafter be described with reference to the accompanying drawings.

FIG. 1 depicts scanning electron micrographs of a 3D printed 40% vol. hBN scaffold. The 3D printed struts are highly uniform and can be printed consistently over relatively large areas. The printed struts can span gaps as seen in the grid inner structure in the scanning electron micrographs. The surface morphology is relatively smooth since the poly(lactic-co-glycolic acid) (PLGA, also referred to as polylactide-co-glycolide (PLG)) polymer uniformly coats and disperses the hBN flakes within the polymer matrix.

FIGS. 2A-2D depict mechanical properties of 3D printed hBN.

FIG. 6D shows the intensity corrected for the amount of PLGA present in the hBN composite. The highest relative crystallinity was observed for the 20% vol. hBN and the lowest relative crystallinity for the 70% vol. hBN. The relative crystallinity of the 3D printed structures was determined by normalizing the PXRD spectra to the primary hBN peak at 26.7° and then measuring the intensity of the primary PLGA peak at 16.9°.

DETAILED DESCRIPTION

Thermal management scaffolds for implantable devices and other devices are provided. Also provided are the devices that utilize the scaffolds for thermal management. The scaffolds for use in implantable biomedical devices are made from composite materials that are thermally conductive, electrically insulating, and cytocompatible. For other applications, the composite materials need not be cytocompatible. As used herein, the term cytocompatible refers to a material that is biocompatible and, more specifically, that does not have an adverse effect on the growth and viability of biological cells. Using 3D extrusion printing, the composite materials can be patterned into the complex, mechanically flexible 3D architectures tailored for use in applications, such as bioelectronic implants.

The cytocompatible scaffolds are composed of a composite material that includes hBN particles dispersed in a biocompatible, elastomeric polymer binder. These composites and scaffolds made from the composites can have high hBN particle contents, while maintaining high mechanical flexibility and stretchability. For example, some embodiments of the composites and the scaffolds have an hBN content in the range from 20 vol. % to 70 vol. %. This includes embodiments of the composites and scaffolds that have an hBN content in the range from 25 vol. % to 60 vol. %, and further includes embodiments of the composites and scaffolds that have an hBN content in the range from 35 vol. % to 45 vol. %.

hBN is composed of hexagonally bonded alternating boron and nitrogen atoms in planar 2D layers, which are stacked together by a combination of van der Waals forces and electrostatic interactions. Although it is electrically insulating, hBN is highly thermally conductive, with a theoretical thermal conductivity as high as 300 W K$^{-1}$ m$^{-1}$ along the basal plane. The hBN particles used in the composite materials described herein can be platelets having lateral dimensions in the range from about 0.1 µm to about 2 µm and thicknesses in the range from about 10 nm to 100 nm. However, hBN particles with dimensions outside of these ranges can also be used.

The loading of the hBN in the composite material can be tailored to provide the material with high thermal conductivity. For example, some embodiments of the composites and scaffolds have a thermal conductivity of at least 1.5 W/m-K. This includes embodiments of the composites and scaffolds that have a thermal conductivity of at least 2 W/m-K. High thermal conductivities can be achieved while maintaining a high degree of mechanical flexibility. By way of illustration, some embodiments of the composites and scaffolds have an elastic modulus of at least 20 MPa. This includes embodiments of the composites and scaffolds that have an elastic modulus of at least 30 MPa. For example, various embodiments of the composite material have an elastic modulus in the range from 30 MPa to 50 MPa.

Suitable biocompatible polymer binders include, for example, biocompatible polyesters, such as polylactic acid, polyglycolic acid, PLGA, polycaprolactone (PCL), or any combination of these.

The flexible and stretchable qualities of the hBN-polymer composite scaffolds, in addition to their cytocompatibility, render them suitable for thermal management applications in implantable electric devices. Implantable devices are biocompatible devices that are sized and shaped for in vitro implantation in a living biological entity, such as a human or other mammal. These devices are designed to interface with biological systems, such as organs, skeletal-, muscular-, and/or nervous systems. Common illustrative examples include cardiac pacemakers, sub-dermal insulin pumps, and sub-dermal microchips or radio-frequency identification (RFID) chips. Bioelectronic devices are desirably designed to be compatible with the thermo-mechanical properties of their physiological environment. Therefore, for implantable devices that generate undesirable waste heat, the thermal management scaffolds can be used to control thermal dissipation to surrounding tissue by placing the implantable devices in contact with the thermal management scaffolds. For example, the thermal dissipation scaffolds can be disposed on or around at least a portion of an implantable electronic device.

Another application for the composite materials and composite fibers described herein is as membrane separators in batteries, such as lithium ion batteries, where membranes composed of one or more of the porous composite fibers can mitigate overheating. Overheating in lithium ion batteries is a significant obstacle to the full adoption of the technology. Overheating can be caused by a short circuit between an anode (e.g., a lithium anode in a lithium ion battery) and a solid or liquid electrolyte. Separators are placed between the anode and the electrolyte to prevent shorting. Alternatively, a separator can be placed between the cathode and the electrolyte. Thermal stability of the membranes is critical. In addition, the membranes must be permeable to ion (e.g., lithium ion) diffusion. Using 3D extrusion printing, the hBN composites can be used to form thermally stable, ion-permeable multilayered membranes composed of continuous and flexible fibers.

One embodiment of a battery includes: an anode; a cathode; an electrolyte in electrical communication with the anode and the cathode; and a membrane separator that separates the electrolyte from either the anode or the cathode. The membrane separator comprising multiple layers of continuous flexible fibers, the continuous flexible fibers composed of a composite material of the type described herein that includes an elastomeric polymer binder; and hexagonal boron nitride particles dispersed in the elastomeric polymer binder.

Yet another illustrative application for the composite materials and composite fibers described herein is as dielectric substrates for antennas, such as radiofrequency and microwave antennas. Using 3D extrusion printing, the hBN composites can be used to form thermally stable and conformal flexible substrates composed of one or more continuous, flexible, heat absorbing fibers. Once the substrates are extruded, metal strips can be formed on a surface of the substrate to form the conductive traces of an antenna. Suitable methods include inkjet printing, sputtering, and attaching metal foil strips to the substrate.

One embodiment of an antenna includes: a dielectric substrate; and electrically conductive traces configured to act as an antenna on a surface of the dielectric substrate. The dielectric substrate comprises one or more continuous flexible fibers, the continuous flexible fibers composed of a composite material of the type described herein that includes an elastomeric polymer binder; and hexagonal boron nitride particles dispersed in the elastomeric polymer binder.

The thermal management scaffolds can be formed from 3D extrusion printable compositions that include the hBN particles, an elastomeric polymer binder, and at least one solvent. For implantable biomedical devices, the elastomeric polymer should be biocompatible. As used herein, the term biocompatible refers to a material that does not have a significant negative impact on tissue growth and viability and that, if implanted in a living biological entity (e.g., a mammal, such as a human), does not cause an adverse reaction in that biological entity. The 3D extrusion printable compositions can be made by dissolving the polymer binder in an organic solvent or a solvent system comprising two or more organic solvents; dispersing the hBN particles into an organic solvent or a solvent system comprising two or more organic solvents; and mixing the polymer solution with the dispersion to form a 3D extrusion printable composition. If two or more different solvents are used in the formulation of the composition, the solvent system may be a graded solvent system, as illustrated in the Example. By way of illustration, suitable solvents for dissolving the polymer and/or dispersing the hBN particles include dichloromethane (DCM), chloroform, ethylene glycol butyl ether, and dibutyl phthalate. In order to render the compositions extrudable through a 3D printing nozzle, enough of the solvent can be allowed to evaporate to provide the composition with a viscosity suitable for 3D extrusion printing. This process can be conducted at room temperature and under atmospheric conditions. Suitable viscosities for 3D printable compositions include viscosities in the range from about 25 Pa·s to about 40 Pa·s at room temperature.

The solvents may include components that act as a plasticizer, such as dibutyl phthalate. The use of the plasticizer can facilitate 3D extrusion of the composition and can increase the elongation of the final material. Moreover, the compositions can be formulated such that the degree of porosity and/or the degree of crystallinity of the extruded composite provides both high thermal conductivity and good mechanical flexibility, as illustrated in the Example. By way of illustration, composite materials having hBN contents of 30 vol. % to 60 vol. %, porosities in the range from 20% to 40%, and having a partially crystalline and partially amorphous character can provide thermal conductivities of 1.5 W/m-K or greater. This result can be achieved using hBN:plasticizer (for example, DBP) mass ratios in the range from 3:1 to 6:1, including in the range from 3.5:1 to 5.5:1 and further including in the range from 4:1 to 5:1. The plasticizer may remain in the extruded composites. However, for applications where the composite needs to be cytocompatible, it should be washed out of the final extruded material.

The resulting compositions are characterized in that they can be 3D extrusion printed into continuous self-supporting fibers (struts) from which self-supporting 3D scaffolds can be built. Self-supporting struts formed by 3D printing the compositions are characterized in that they substantially retain the 3D shape imparted to them by the extrusion process. As such, the struts will typically have a round or oval cross-sectional shape, and the cross-sectional diameters of the struts will reflect the aperture size through which they were extruded. By way of illustration only, some embodiments of the thermal management scaffolds will be formed from struts having cross-sectional diameters in the range from 50 µm to 500 µm, although diameters outside of these ranges can be used. The struts may be porous, with strut porosities of at least 20%, for example. Extrusion through a nozzle ensures that the struts will have a substantially uniform cross-section along their lengths. (In this context "substantially uniform" is used in recognition that the extrusion process is not perfect and may result in some cross-sectional non-uniformity based on the limitations of the printing equipment. Therefore, a printed strut having a cross-sectional diameter that varies by no more than ±30% along its length, is considered to have a substantially uniform cross-section along its length. This includes struts having a cross-sectional diameter that varies by no more than ±20%, no more than ±10%, or no more than ±5% along its length.)

When the compositions are extruded, the elastomeric binders provide for the formation of extruded struts that are continuous, flexible, and strong. In addition, the elastomeric properties of the polymer binders impart the thermal management scaffolds that are formed from the struts' elastic mechanical properties, which allow them to 'bounce back' to their original shape after undergoing loading (e.g., compression or tension).

Figure 1:
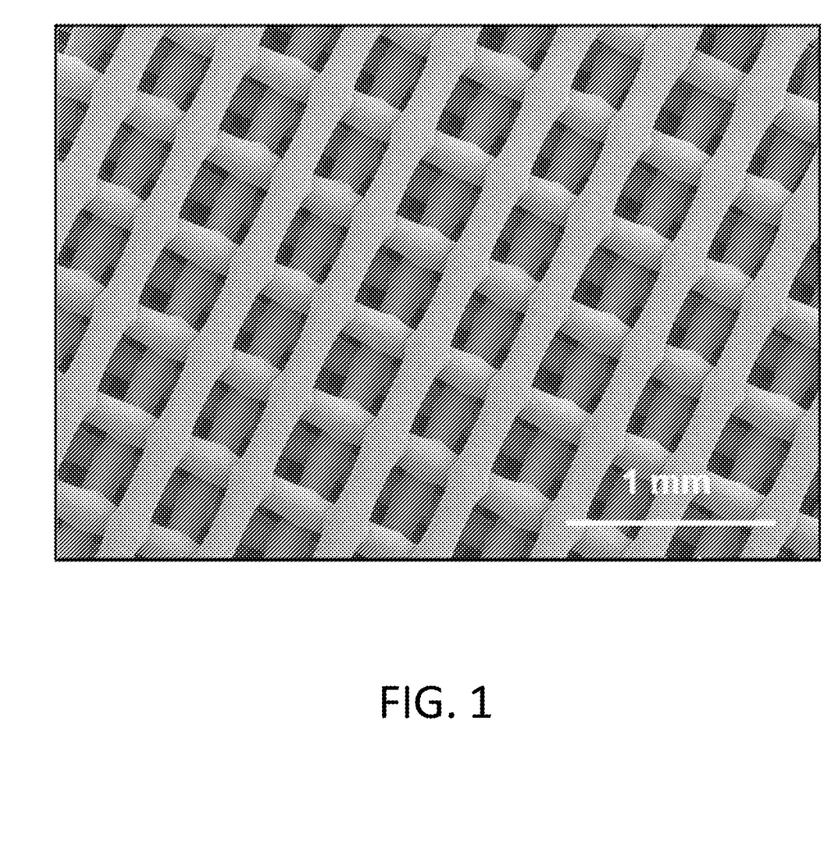
Figure 2A:
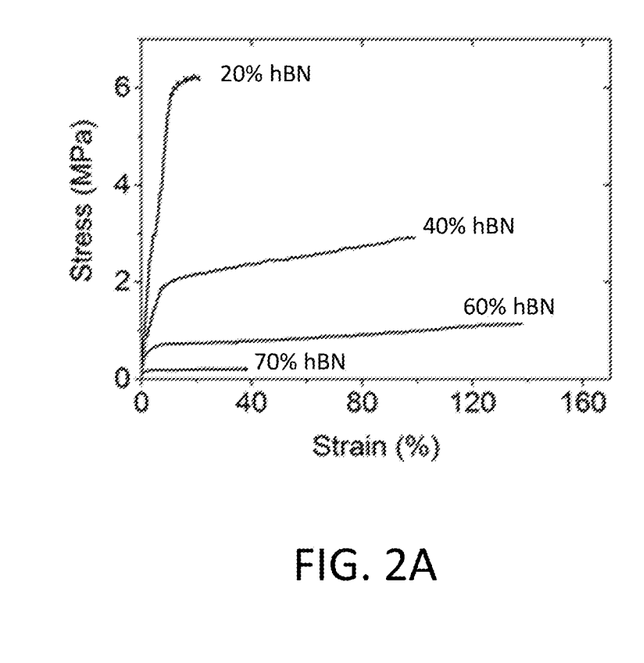
FIG. 2A shows tensile testing stress-strain curves for 3D printed samples with varying hBN loading.
Figure 2B:
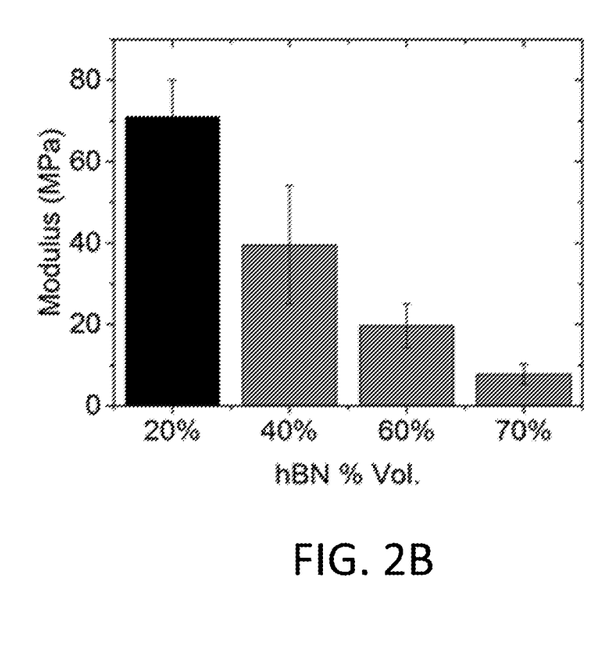
FIGS. 2B-2D show corresponding (FIG. 2B) modulus, (FIG. 2C) strain to failure, and (FIG. 2D) tensile strength values (n≥3) extracted from the tensile testing stress-strain characterization. Tensile strength and modulus are significantly different ($p<0.05$) for each composition. Strain to failure of the 40% vol. hBN and 60% vol. hBN samples are significantly higher ($p<0.05$) than the strain to failure for the 20% vol. hBN and 70% vol. hBN samples. Error bars represent one standard deviation.
Figure 2C:
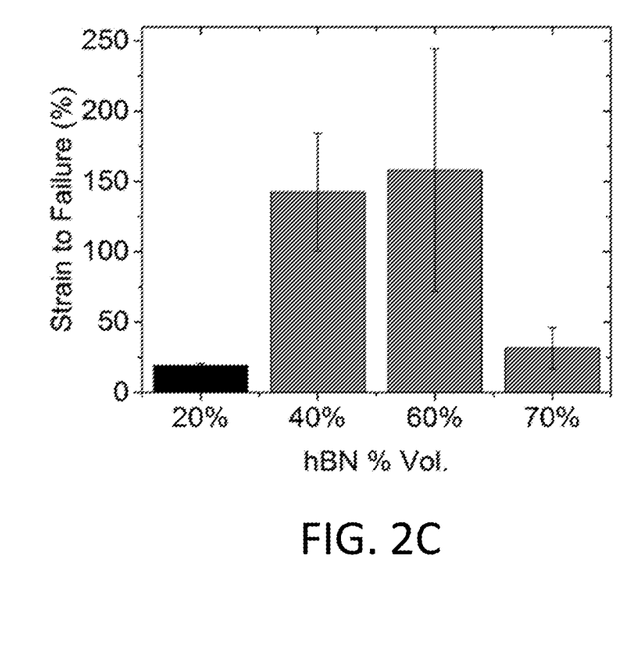
Figure 2D:
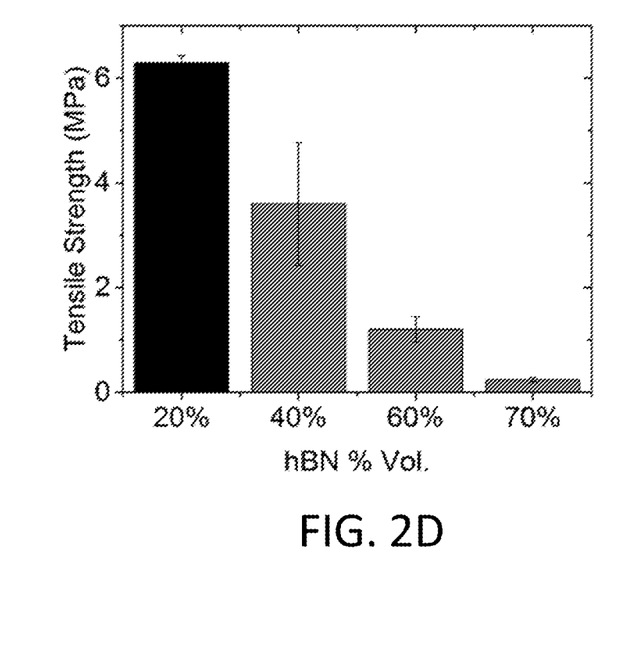

Porous or non-porous scaffolds can be printed via strut-by-strut and/or layer-by-layer extrusion of a 3D extrusion printable composition through the nozzle of a bioplotter. Scaffolds can be built from a plurality of discrete struts and/or from a strut that is folded back and forth onto itself. The use of 3D printing for the fabrication of the thermal management scaffolds is advantageous because it provides for regular geometric patterning of one or more strut layers that make up the scaffold. For example, a thermal management scaffold may include one or more layers, each of the layers comprising a plurality of struts running substantially parallel with one another or comprising a single strut that is folded into, for example, an s-shape or zig-zag, within the plane of the layer. For scaffolds that include more than one such layer, the struts in neighboring layers may be misaligned (with respect to their longitudinal axes), such that the layers form a grid, as illustrated in FIG. 1. Neighboring struts may be separated by a gap or directly adjacent and even merged at their interfaces.

In a grid comprising a regular arrangement of struts, the struts in a layer can be spaced apart and substantially aligned along their long axes. (In this context "substantially aligned" is used in recognition that the extrusion process is not perfect and may result in some minor non-uniformity in the alignment of the struts based on the limitations of the printing equipment. Therefore, neighboring struts separated by a spacing that varies by no more than ±30% along the lengths of the struts, are considered to be substantially aligned. This includes struts having a spacing that varies by no more than ±20%, no more than ±10% or no more than ±5% along their lengths.) If the struts are straight, this results in a layer comprising a series of substantially parallel struts. In such a regular arrangement of struts, the struts in adjacent layers may be extruded at angles ranging from 0° to 360° with respect to each other to form a regular grid pattern, as shown in FIG. 1. For the purpose of this disclosure, the angle defined between a strut in one layer and a strut in an adjacent layer in a layered stack is referred to as the advancing angle. By way of illustration, an advancing angle of 90° can be used to form a regular square grid, as shown in FIG. 1. Alternatively, the struts in different layers can be extruded at smaller advancing angles to provide a scaffold having a more tortuous pore arrangement.

EXAMPLE

This example presents a 3D printable hBN-polymer ink that contains only two solid components: hBN and PLGA, which is an elastomer that acts as a biocompatible polymer binder for the functional hBN particles. The PLGA and hBN particles are dissolved and dispersed, respectively, within a tri-solvent system: dibutyl phthalate (DBP) is used as a plasticizer; ethylene glycol monobutyl ether (EGBE) is used as a surfactant to disperse the hBN particles; and DCM is a high volatility solvent that dissolves the PLGA and provides the mechanism for solidification during the printing process. Due to its high vapor pressure in addition to the high surface area that is created upon extrusion, the DCM evaporates rapidly, resulting in a solid construct. During this 3D printing process, the PLGA precipitates and condenses around the hBN particles, resulting in a well-defined printed strut that is self-supporting (FIG. 1). The printed struts are uniform in size and span gaps of several millimeters without noticeable sagging or deformation, allowing for the creation of complex geometries with well-controlled porosity.

The 3D printed hBN constructs are highly robust mechanically, allowing for direct handling immediately following printing. In addition, the hBN scaffolds are flexible and can be cut, folded, or rolled while still maintaining their mechanical integrity, which allows for the possibility of additional manipulation of the constructs after printing in order to achieve an even wider range of sizes and geometries. For a quantitative assessment of the mechanical properties, tensile testing was performed for a range of hBN loadings, which are reported as a volume fraction of the solid components (FIGS. 2A-2D). The formulations are provided in Table 1.

TABLE 1

Example ink formulations for 3D printed hBN.

| Sample Name | hBN (g) | PLGA (g) | EGBE (g) | DBP (g) |
|---|---|---|---|---|
| 20% vol. hBN | 0.84 | 1.84 | 0.36 | 0.18 |
| 40% vol. hBN | 1.68 | 1.38 | 0.72 | 0.36 |
| 60% vol. hBN | 2.52 | 0.92 | 1.08 | 0.54 |
| 70% vol. hBN | 2.94 | 0.69 | 1.26 | 0.63 |

Figure 5:
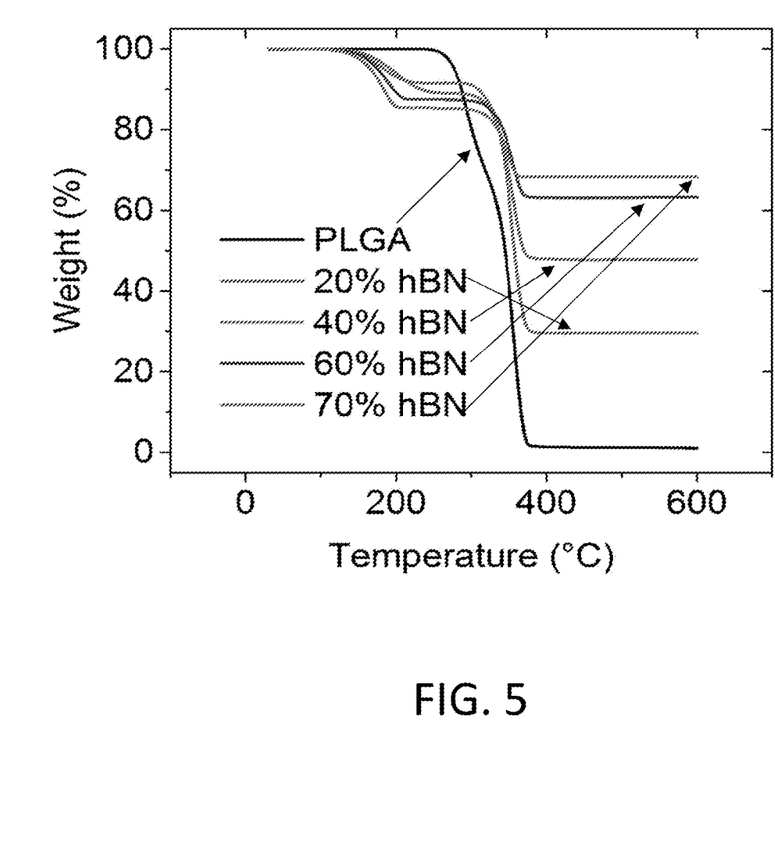
FIG. 5 depicts thermogravimetric analysis (TGA) scans of 3D printed hBN with varying hBN:PLGA composition ratios. The PLGA curve is the raw PLGA polymer pellets used in the ink formulations (i.e., no solvents). Samples were heated from 30° C. to 600° C. at a heating rate of 5° C./minute in a nitrogen environment.
Figure 6A:
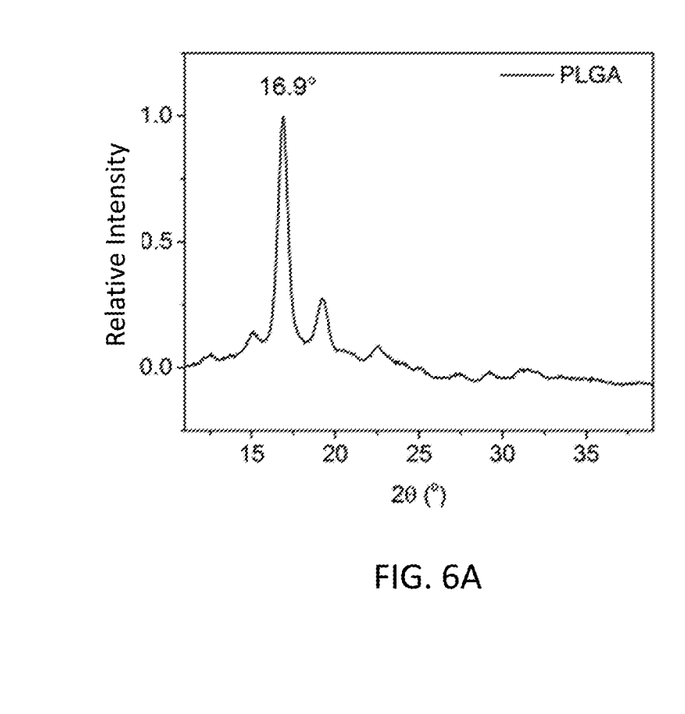
FIGS. 6A-6C depict powder X-ray diffraction (PXRD) scans of (FIG. 6A) raw PLGA, (FIG. 6B) raw hBN powder, and (FIG. 6C) 3D printed hBN with varying hBN:PLGA composition ratios to determine the relative crystallinity of the PLGA polymer matrix.
Figure 6B:
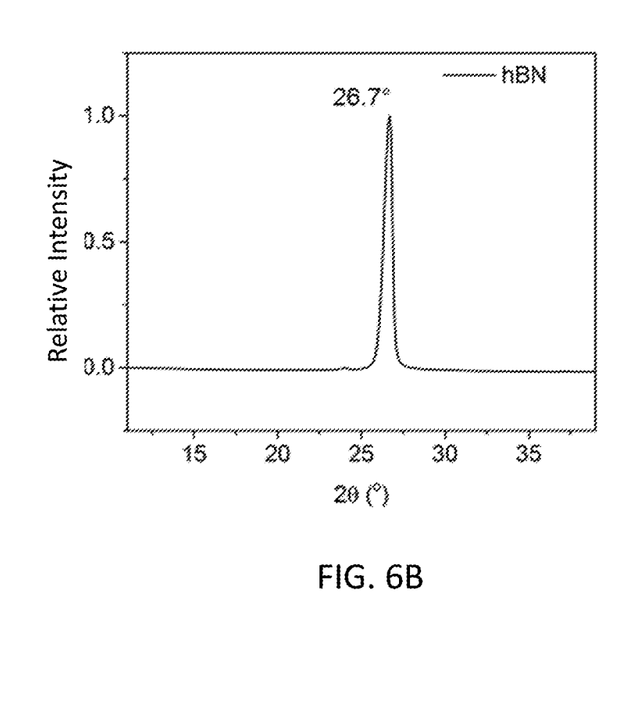
Figure 6C:
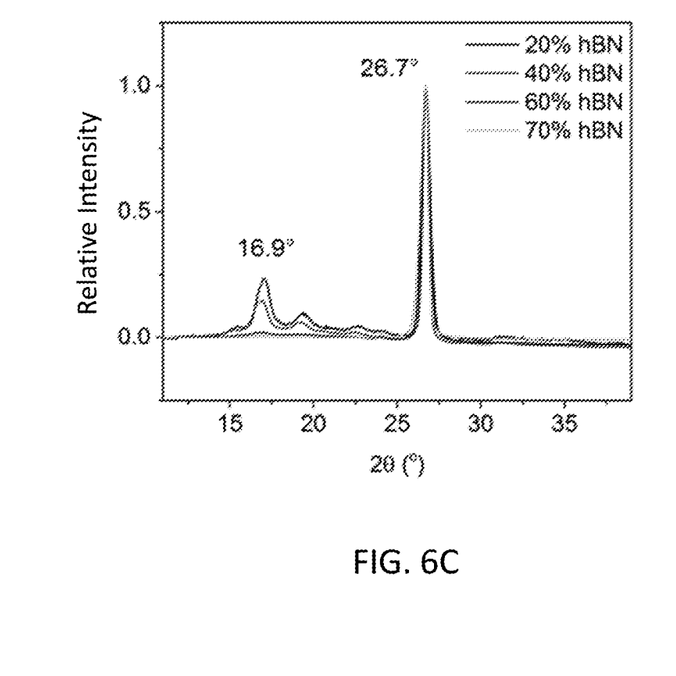
Figure 6D:
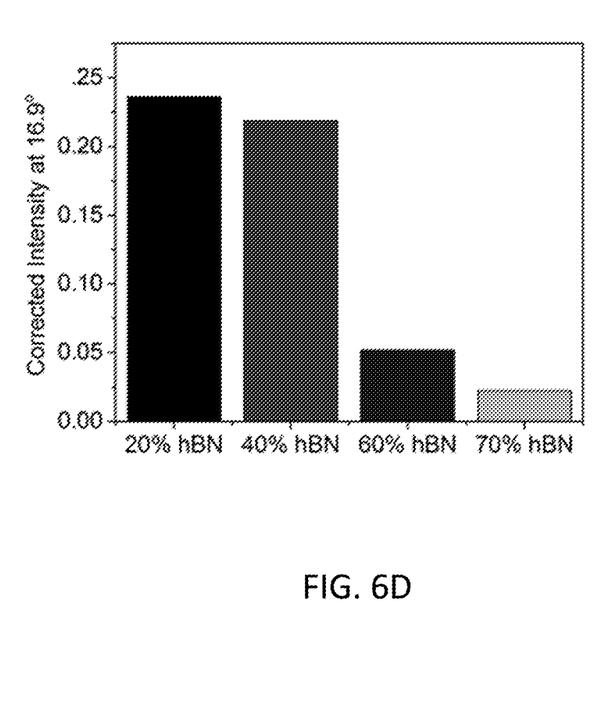

The tensile strength of the 3D printed constructs decreases significantly as the amount of hBN increases due to the decreasing amount of polymer present, which bears the majority of the tensile load. The amount of plasticizer added to the ink formulation is directly proportional to the amount of hBN to help improve fluidity and prevent clogging during the printing process, and the plasticizer is still present in the resulting 3D printed constructs (FIG. 5, Table 2). Consequently, the elastic modulus shows a similar trend, where the 3D printed constructs become less stiff with higher hBN content due to the increasing amount of plasticizer.

TABLE 2

Compositions of 3D printed hBN based on the TGA scans shown in FIG. 5. The volume percent reported in the last two columns of the table takes into account only the solid components of the 3D printed hBN (i.e., hBN and PLGA).

| Sample Name | Weight % solvents | Weight % hBN | Weight % PLGA | Volume % hBN | Volume % PLGA |
|---|---|---|---|---|---|
| 20% vol. hBN | 8.4 | 29.7 | 61.9 | 20.8 | 79.2 |
| 40% vol. hBN | 10.8 | 47.8 | 41.5 | 38.7 | 61.3 |
| 60% vol. hBN | 12.6 | 63.2 | 24.3 | 58.8 | 41.2 |
| 70% vol. hBN | 14.7 | 68.3 | 17.0 | 68.7 | 31.3 |

The elongation to failure of the 3D printed constructs initially increases with increasing hBN content and then sharply declines when the hBN loading is increased from 60% to 70%. The initial increase in ductility is likely due to the presence of increasing amounts of plasticizer, which tracks proportionally with the hBN content and the crystal structure of the polymer, which was found to vary as a function of hBN content (FIG. 6A-6D). In particular, when more polymer is present in the ink, the DCM evaporates more slowly during the printing process, resulting in a more crystalline polymer structure and thus a stiffer, more brittle material. On the other hand, for high fractions of hBN and correspondingly low fractions of polymer, the solvent evaporation occurs more quickly, leading to a more porous scaffold with a more amorphous polymer structure that facilitates increased elongation. The presence of high levels of plasticizer may also inhibit the ordering of the polymer chains at high hBN loadings, which would further decrease polymer crystallinity. It should be noted that eventually a limit is reached where there is an insufficient amount of polymer to adequately coat the hBN particles, resulting in a soft, brittle material, as observed for the case of 70% vol. hBN. Overall, by controlling the composition and trisolvent ink formulation, a wide range of mechanical properties can be achieved for 3D printed hBN constructs to meet the needs of specific applications.

One such application is the use of 3D printable hBN as a thermal interface material. Due to the high thermal conductivity of the hBN filler, the overall thermal conductivity of the polymer nanocomposite will be expected to be enhanced with the addition of hBN. The thermal conductivity of the 3D printed constructs was calculated using Equation 1, where k is the thermal conductivity, $\alpha$ is the measured thermal diffusivity, $\rho$ is the measured density, and $c_p$ is the measured specific heat capacity:

$$k = \alpha \rho c_p \qquad (1)$$

Figure 3A:
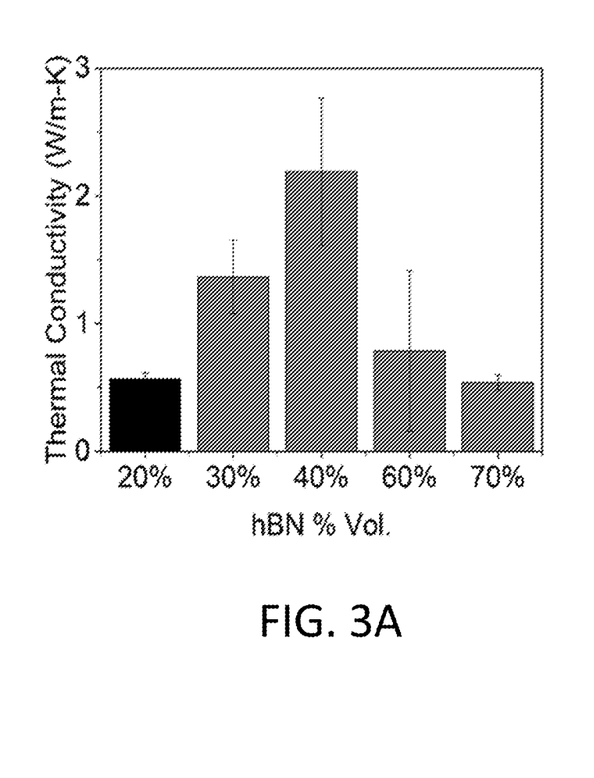
FIGS. 3A-3B depict (FIG. 3A) thermal conductivity and (FIG. 3B) porosity of 3D printed constructs (n=3) for different hBN loading. Thermal conductivity for the 20%, 30%, and 40% vol. hBN samples are significantly different from each other ($p<0.05$), while there is no significant difference between the 20%, 60%, and 70% vol. hBN samples. The porosity is significantly higher ($p<0.05$) for the 60% and 70% vol. hBN constructs, while the porosity does not vary significantly between the 20%, 30%, and 40% vol. hBN constructs. The thermal conductivity increases as a function of hBN content until a significant increase in the porosity of the scaffolds causes a disruption in the thermally conductive network. Porosity was determined by comparison of the theoretical density to the experimentally measured density of the constructs. Error bars represent one standard deviation.
Figure 3B:
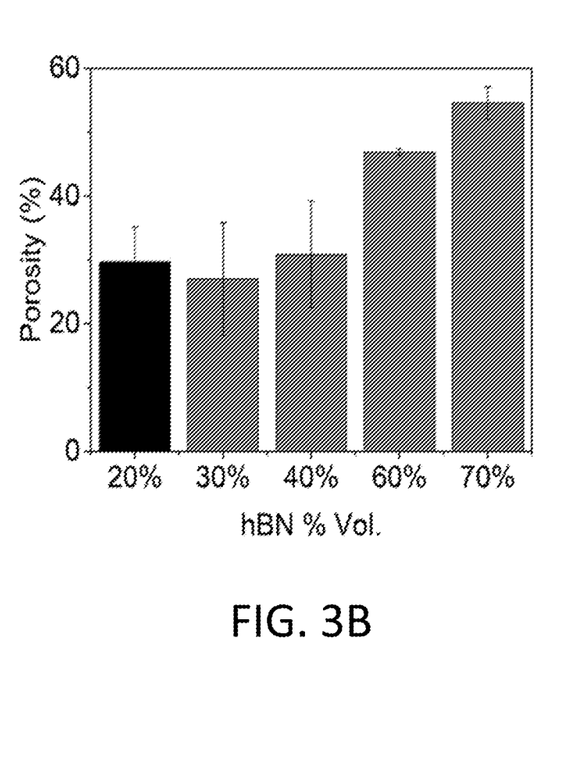

The resulting thermal conductivities are shown in FIG. 3A. The thermal conductivity of the 3D printed materials initially increases with increasing hBN content as expected. However, above a threshold, the thermal conductivity of the constructs begins to decrease despite the high hBN loading. This reduction in the thermal conductivity correlates with a significant change in the microstructure of the 3D printed constructs at high hBN loadings, which is apparent from cross-sectional scanning electron microscopy (SEM) of the constructs. Specifically, due to the rapid evaporation of DCM for high loading hBN inks, the porosity of the printed structure increases (FIG. 3B). This increased porosity likely leads to the observed decrease in thermal conductivity since the pores not only disrupt the percolation of the hBN particles, but also act as a thermal insulator within the polymer matrix. Nevertheless, at the optimal loading of 40% vol. hBN, the thermal conductivity reaches 2.1 W K$^{-1}$ m$^{-1}$, which is suitable for many thermal management applications.

Porosity was determined by comparing the theoretical density of the material to the experimentally measured density of the constructs. Theoretical density was calculated based on the composition of the printed structure. Experimental density was determined by measuring the mass and the volume of the printed structure (printed as a solid cube).

Figure 4:
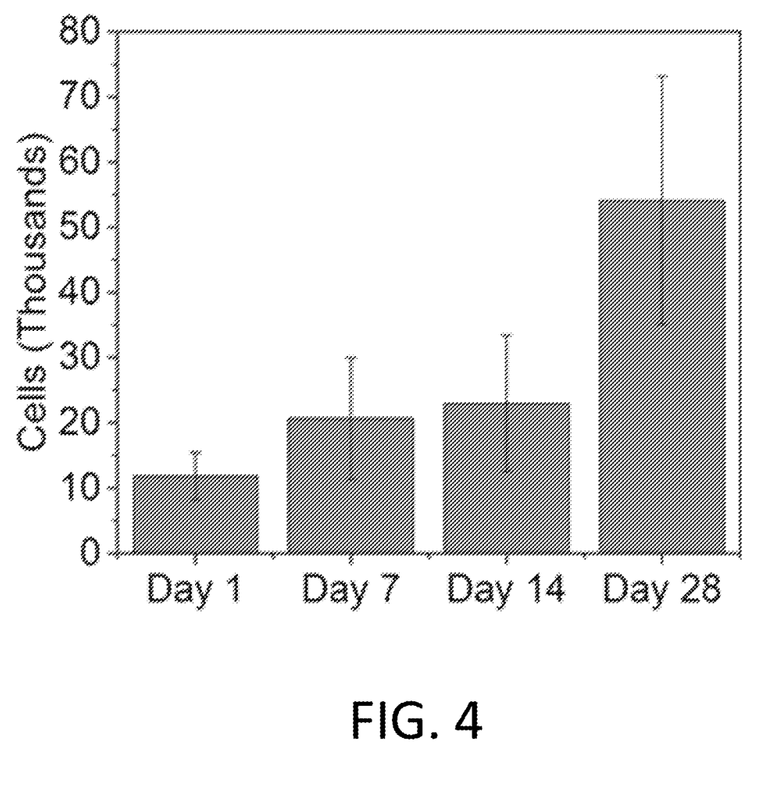
FIG. 4 depicts DNA quantification of hMSCs seeded onto 40% vol. hBN scaffolds (n=3) over 28 days. Error bars represent one standard deviation.

For biomedical applications, hBN also potentially offers advantages as a polymer nanocomposite filler due to its biocompatibility in vitro. By using a biocompatible polymer matrix in this 3D printable hBN formulation, the material can be made suitable for integration into implantable devices. To confirm cytocompatibility, constructs of varying hBN content (20%, 40%, and 60% vol.) were 3D printed into sheets 6 layers thick and then cut into 5 mm cylinder scaffolds and rinsed with ethanol to remove residual solvents. Passage 2 female bone-marrow-derived human mesenchymal stem cells (hMSCs) were purchased and extended to passage 5 before seeding onto the hBN scaffolds. The growth and proliferation of the hMSCs on the scaffolds in Dulbecco's modified Eagle's medium (DMEM) were evaluated at multiple time points over 4 weeks using a live/dead stain and confocal imaging. This growth was further quantified using a double-stranded DNA (dsDNA) quantification assay (FIG. 4). The cellular attachment and morphology of the cells were further characterized using scanning electron microscopy. Already at day 1, a favorable interaction of the cells with the 40% vol. hBN scaffold was observed as the cells attached and spread out on the surface of the scaffold. Over the course of 4 weeks, high viability, growth, and proliferation of the hMSCs were also observed qualitatively through live/dead staining on scaffolds containing 20% vol. and 60% vol. hBN. The healthy growth of the cells resulted in the formation of an extracellular matrix and the ability of the cells to span gaps and pores within the scaffold. The high cytocompatibility of these 3D printable hBN constructs offers a distinct advantage for thermal applications, specifically in bioelectronics.

Experimental Details

Ink Preparation and Printing: Poly(lactic-co-glycolic acid) (82:18) copolymer (Evonik), hexagonal boron nitride powder (MilliporeSigma), dichloromethane (MilliporeSigma), ethylene glycol butyl ether (MilliporeSigma), and dibutyl phthalate (MilliporeSigma) were all used as received. To prepare the inks, PLGA was dissolved in DCM and then added to a mixture of hBN, EGBE, and DBP. Five different volume ratios of solid components were prepared and characterized ranging from 20% vol. hBN to 70% vol. hBN. Due to the high-volume fraction of particles in these inks, the amount of EGBE and DBP added to the ink formulations was proportional to the amount of hBN present in order to keep the hBN particles well dispersed and prevent clogging of the nozzle. DCM was added in excess and then allowed to evaporate under ambient conditions until a viscosity of ~30 Pa·s was achieved. All samples were printed using a 3D BioPlotter (EnvisionTEC GmbH). Depending on the composition and the tip diameter, the printing speed was varied in the range 5-20 mm s$^{-1}$, and the printing pressure was varied in the range 0.5-3.0 bar.

Mechanical Characterization: Tensile testing was performed to determine the mechanical properties of the 3D printed scaffolds. Solid tensile bars with a gauge length of 20 mm and cross-sectional area of 3 mm$^2$ were printed using a 250 μm tip. Tensile tests (LF Plus mechanical tester, Lloyd Instruments) were performed at an extension rate of 2 mm/min.

Thermal Characterization: The thermal diffusivity was measured using laser flash analysis (Netzch LFA 457) following a Cowan with a pulse correction model and a linear baseline. Solid films of material were 3D printed and then heated under vacuum for one hour at 50° C. to remove the remaining solvent preceding measurement. The measurements were performed at 65° C. under vacuum using a graphite coating as per Netzch's recommendations to mitigate the translucent nature of the polymer. The measurements were performed with the laser pulse perpendicular to the printed filament, as the experiments showed a lack of anisotropic thermal conductivity. The density was determined by measuring the mass and geometric volume of the printed samples. The specific heat capacity of each sample was determined using differential scanning calorimetry (DSC822e Differential Scanning calorimeter, Mettler Toledo) using the well-established sapphire method. (See, e.g., O'Neill, M. J. *Anal. Chem.* 1966, 38, 1331-1336.) In this method, the mass-corrected DSC signal of a sample across the temperature range of 60° C. to 70° C. was compared to that of a sapphire standard undergoing the same temperate profile.

In Vitro Cytocompatibility: For in vitro cytocompatibility studies, 2 cm×2 cm boxes of 6 layers with an internal structure of 90° offset grids with a 0.5 mm distance between the center of the struts were printed using a 250 μm tip. 5 mm cylinders were punched out using a biopsy punch and then rinsed with ethanol and sterile PBS before seeding with hMSCs. Compatibility with hMSCs was established using a method described previously. (See, e.g., Jakus, A. E., et al., *ACS Nano* 2015, 9, 4636-4648.) Briefly, passage 2 hMSCs were purchased from Lonza, extended to passage 5, and then seeded onto the hBN scaffolds (~25,000 cells per scaffold) in DMEM. Viability was established using a live/dead stain (Invitrogen) and imaged using a Nikon C2+ Laser Scanning Confocal Microscope. Following live/dead imaging, the scaffolds were fixed for SEM imaging using an aqueous solution of 3% sucrose and 2% gluteraldehyde for 15 minutes. The scaffolds were then dehydrated using a series of increasing ethanol concentrations followed by critical point drying (Samdri 795 Critical Point Dryer) and then coated with 15 nm of osmium before SEM imaging (Hitachi SU8030). The quantification of cells was determined using Quanti-iT Picogreen dsDNA Assay Kit (Invitrogen) at 1, 7, 14, and 28 days after lysing the cells by gentle bath sonication of the scaffolds (in 0.02% Triton X100 detergent). The fluorescence was measured at an excitation of 485 nm and emission of 535 nm using a Cytation 3 Plate Reader.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more."

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A biocompatible device comprising:
    an implantable electronic device; and
    a thermally conductive, electrically insulating scaffold around at least a portion of the implantable electronic device, the scaffold comprising continuous flexible fibers of a cytocompatible composite, the cytocompatible composite comprising:
        a biocompatible elastomeric polymer binder; and
        hexagonal boron nitride particles dispersed in the biocompatible elastomeric polymer binder.

2. The device of claim 1, wherein the cytocompatible composite has a hexagonal boron nitride particle content in the range from 30 vol. % to 60 vol. %.

3. The device of claim 1, wherein the cytocompatible composite has a hexagonal boron nitride particle content in the range from 35 vol. % to 45 vol. %.

4. The device of claim 1, wherein the cytocompatible composite has a porosity in the range from 20% to 40%.

5. The device of claim 1, wherein the cytocompatible composite has a porosity in the range from 20% to 35%.

6. The device of claim 2, wherein the cytocompatible composite has a porosity in the range from 20% to 40%.

7. The device of claim 6, wherein the biocompatible elastomeric polymer binder is poly(lactic-co-glycolic acid).

8. The device of claim 7, wherein the cytocompatible composite has a thermal conductivity of at least 1.5 W/m-K.

9. The device of claim 1, wherein the one or more fibers have a cross-sectional diameter in the range from 50 μm to 500 μm.

10. The device of claim 9, wherein the one or more fibers have a circular or oval cross-section.

* * * * *